United States Patent
Berglund et al.

(10) Patent No.: US 9,662,078 B2
(45) Date of Patent: May 30, 2017

(54) METHOD AND DEVICE FOR GENERATING AN ENERGY-RESOLVED X-RAY IMAGE WITH ADAPTED ENERGY THRESHOLD

(71) Applicant: KONINKLIJKE PHILIPS N. V., Eindhoven (NL)

(72) Inventors: Henning Per Johan Berglund, Sundbyberg (SE); Jon Erik Fredenberg, Vallentuna (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/773,506

(22) PCT Filed: Sep. 25, 2014

(86) PCT No.: PCT/EP2014/070422
§ 371 (c)(1),
(2) Date: Sep. 8, 2015

(87) PCT Pub. No.: WO2015/052000
PCT Pub. Date: Apr. 16, 2015

(65) Prior Publication Data
US 2016/0206256 A1    Jul. 21, 2016

(30) Foreign Application Priority Data
Oct. 9, 2013 (EP) .................... 13187813

(51) Int. Cl.
*A61B 6/00* (2006.01)
*G01T 1/29* (2006.01)
*A61B 6/03* (2006.01)

(52) U.S. Cl.
CPC ............ *A61B 6/4241* (2013.01); *A61B 6/032* (2013.01); *A61B 6/4233* (2013.01); *A61B 6/502* (2013.01); *G01T 1/2985* (2013.01)

(58) Field of Classification Search
CPC ...................................................... A61B 6/482
See application file for complete search history.

(56) References Cited

U.S. PATENT DOCUMENTS

| 8,442,184 B2 | 5/2013 | Forthmann et al. |
| 2007/0147574 A1 | 6/2007 | De Man et al. |

(Continued)

FOREIGN PATENT DOCUMENTS

| JP | 2001-74844 | 3/2001 |
| JP | 2008-224609 | 9/2008 |

(Continued)

OTHER PUBLICATIONS

Aslund, M., et al.; AEC for scanning digital mammography based on variation of scan velocity; 2005; Med. Phys.; 32: 3367-3374.
(Continued)

*Primary Examiner* — Dani Fox (57) ABSTRACT

A method for generating an energy-resolved X-ray image is proposed, usable e.g. for mammography or CT applications. First, a preferably low-dose X-ray beam (5) is directed through a region of interest of an object (15) such as a female breast and initial X-ray intensity values are acquired. Based on these initial X-ray intensity values, energy threshold values of for example a photon-counting energy-resolving X-ray detector (9) are specifically adapted to local properties and features of the object (15). With such adapted energy threshold values, energy-resolved main X-ray intensity values are acquired for finally generating the energy-resolved X-ray image. The principle of such specific adapting of energy threshold values in energy-resolved X-ray image acquisition may be advantageously implemented in scanning X-ray systems wherein first detector elements (17) of a scanned X-ray detector (9) are used to acquire the initial X-ray intensity values in order to then set the energy (Continued)

threshold values for subsequent detector elements (17) with which main X-ray intensity values are acquired.

19 Claims, 4 Drawing Sheets

(56) References Cited

U.S. PATENT DOCUMENTS

| | | |
|---|---|---|
| 2009/0268862 A1 | 10/2009 | Ziegler |
| 2010/0232669 A1 | 9/2010 | Ziegler et al. |
| 2010/0301224 A1 | 12/2010 | Morel et al. |
| 2011/0081071 A1 | 4/2011 | Benson et al. |
| 2012/0087463 A1 | 4/2012 | Greenberg et al. |
| 2014/0270073 A1* | 9/2014 | Spahn ............... G01N 23/04 378/62 |

FOREIGN PATENT DOCUMENTS

| | | |
|---|---|---|
| JP | 2009-219610 | 10/2009 |
| WO | 02/22018 | 3/2002 |
| WO | 2012/144589 | 10/2012 |
| WO | 2013093684 A2 | 6/2013 |

OTHER PUBLICATIONS

Aslund, M., et al.; Physical characterization of a scanning photon counting digital mammography system based on Si-strip detectors; 2007; Med. Phys.; 34:1918-1925.

Cahn, R. N., et al.; Detective quantum efficiency dependence on x-ray energy weighting in mammography; 1999; Med. Phys.; 26(12)2680-2683.

Fredenberg, E., et al.; Measurement of breast-tissue x-ray attenuation by spectral mammography: first results on cyst fluid; 2013; Phys. Med. Biol.; 58:8609-8620.

Fredenberg, E., et al.; Energy resolution of a photon-counting silicon strip detector; 2010; Nuclear Instruments and Methods in Physics Research, Section A; pp. 156-162.

Fredenberg, E., et al.; Observer model optimization of a spectral mammography system; 2010; Medical Imaging; Proc. SPIE 7622.

Fredenberg, E., et al.; Optimization of mammography with respect to anatomical noise; 2011; Medical Imaging; Proc. SPIE 7961.

Norell, B., et al.; Lesion characterization using spectral mammography; 2012; Medical Imaging; Proc. SPIE 8313.

Taibi, A., et al.; Dual-energy imaging in full-field digital mammography: a phantom study; 2003; Phys. Med. Biol.; 48: 1945-1956.

Tapiovaara, M. J., et al.; SNR and DQE analysis of broad spectrum X-ray imaging; 1985; Physics in Medicine and Biology; 30(6)519-529.

* cited by examiner

METHOD AND DEVICE FOR GENERATING AN ENERGY-RESOLVED X-RAY IMAGE WITH ADAPTED ENERGY THRESHOLD

FIELD OF THE INVENTION

The present invention relates to a method for generating an energy-resolved X-ray image comprising a multiplicity of pixels, particularly for mammography or computer tomography applications. Furthermore, the invention relates to a device for performing such method, to a computer program product controlling such method and to a computer readable medium having such computer program product stored thereon.

BACKGROUND OF THE INVENTION

X-ray imaging is used in a wide variety of applications. Therein, an X-ray beam coming from an X-ray source is typically directed through a region of interest of an object and an X-ray detector is used to detect X-ray intensity of the X-ray beam after being transmitted through the object.

Generally, a generated X-ray image comprises a multiplicity of pixels arranged in a 2-dimensional matrix. For each of the pixels an X-ray intensity value is acquired using e.g. an X-ray detector. The X-ray detector may comprise one or a plurality of detector elements. For example, a number of detector elements may be identical to a number of pixels of the image and each detector element of the plurality of detector elements may acquire an X-ray intensity value for one of the pixels of the image. Alternatively, the detector comprises only a small number of detector elements compared to the number of pixels and may be scanned along a region of interest in order to acquire X-ray intensity values for each of the pixels of the image successively.

For example, the X-ray intensity values may be acquired simultaneously for each of these pixels, using an X-ray detector comprising a 2-dimensional matrix array of X-ray detector elements. Therein, for example each single X-ray detector element may provide the X-ray intensity value for one image pixel or a sum of signals from several X-ray detector elements may provide the X-ray intensity value for one single image pixel.

Alternatively, the X-ray intensity values for the multiple pixels may be acquired sequentially by scanning the X-ray beam and/or the X-ray detector through the region of interest. Therein, the detector may have one or a small number of detector elements which acquire X-ray intensity values for one single or a small number of pixels in one step and which is then scanned to a next position.

X-ray imaging may be particularly beneficial for medical applications. Therein, various interior structures in a body of a patient may be examined as such interior structures generally have different X-ray absorbing properties. For example, in mammography applications, structures within the tissue of a female breast may be examined in order to find any malicious tissue.

Energy-resolving X-ray imaging systems have been developed and are now becoming feasible for routine screening and clinical use. Such imaging systems are adapted for discriminating between photon energies of detected X-rays and hence access spectral X-ray information. In such energy-resolving X-ray imaging systems, an X-ray detector may not only measure an overall X-ray intensity impinging onto one of its detector elements but may furthermore be adapted to discriminate between the energies, i.e. the wavelength spectrum, of photons providing such impinging X-ray intensity.

For example, in energy-resolved X-ray imaging, one or several energy threshold value(s) or wavelength threshold value(s) may be predetermined before X-ray examination and during actual X-ray image acquisition a detector may then distinguish between portions of an entire impinging X-ray intensity having photon energies or wavelengths below such threshold value(s) and other portions of the overall X-ray intensity having photon energies/wavelengths above such threshold value(s). Such information may be valuable for subsequent image interpretation.

US 2010/232669 A1 discloses a method for dynamically optimizing the signal-to-noise ratio of attenuation data related to two different X-ray energies for reconstructing an image of an object under examination. The method comprises (a) estimating the thickness and the material composition of the object at a plurality of different projection angles, (b) for each of the various projection angles calculating for a variety of combinations of different first and second X-ray energies a corresponding common signal-to-noise ratio, (c) for each of the various projection angles choosing the first and the second X-ray energy causing the maximum corresponding common signal-to-noise ratio, and (d); for each of the various projection angles acquiring X-ray attenuation data of the object whereby the two X-ray energies are the X-ray energies causing a maximum signal-to-noise ratio assigned to the respective projection angle.

US 2010/301224 A1 discloses an X-ray imaging device including a polychromatic X-ray source and a detector having pixels suitable for operating in photon counting mode within at least one energy window bounded by at least one adjustable threshold, and at least one counter so that each pixel delivers an output dependent on the number of photons received by the pixel in the energy windows during a predetermined time interval. U.S. Pat. No. 8,442,184 A1 discloses a spectral CT with an energy-resolving detector array. WO 2013/093684 A2 discloses a photon-counting X-ray detector. US 2012/0087463 A1 discloses photon counting and energy discriminating detector threshold calibration.

The quality of an energy-resolved X-ray image and particularly of information about the spectral information comprised therein may depend on the specific setting of the threshold values. For example, improper setting of such threshold values may result in acquired energy-resolved X-ray images showing excessive noise. However, optimizing the setting of such threshold values has been found to be non-trivial as e.g. the object properties may vary substantially over the area or volume being imaged.

SUMMARY OF THE INVENTION

There may be a need for a method for generating an energy-resolved X-ray image with high image quality resulting from optimized energy threshold value settings preferably for all points in the image. Furthermore, there may be a need for a corresponding device for generating energy-resolved X-ray images as well as for a computer program product instructing a computer to control such energy-resolved X-ray imaging method and a computer readable medium comprising such computer program product.

According to a first aspect of the present invention, a method for generating an optimized energy-resolved X-ray image comprising a multiplicity of pixels is described. The method comprises the steps of: (a) directing an X-ray beam through a region of interest of an object and acquiring initial X-ray intensity values of X-rays transmitted through the region of interest for each of the pixels; (b) adapting at least one energy threshold value in dependence of the acquired X-ray intensity values for each of the pixels; and (c) directing an X-ray beam having an X-ray spectrum through the region of interest of the object and acquiring first main X-ray intensity values of X-rays transmitted through the region of interest within a first partial X-ray spectrum range at energies below the adapted energy threshold value and acquiring second main X-ray intensity values of X-rays transmitted through the region of interest within a second partial X-ray spectrum range at energies above the adapted energy threshold value for each of the pixels, respectively. Finally, the energy-resolved X-ray image is generated based on the first and second main X-ray intensity values for each of the pixels.

A second aspect of the present invention relates to a device for generating an energy-resolved X-ray image comprising a multiplicity of pixels, wherein the device is adapted for performing the method according to the above first aspect of the invention.

A third aspect of the invention relates to a computer program product comprising computer readable instructions which, when executed on a computer, control a method according to the above first aspect of the invention.

A fourth aspect of the invention relates to a computer readable medium having a computer program product according to the above third aspect of the invention stored thereon.

Without restricting the scope of the invention, a concept of the invention may be understood as being based on the following observations and ideas:

For acquiring an energy-resolved X-ray image, at least one energy threshold value has to be set such that during actual detecting of X-rays transmitted through a region of interest of an object using the threshold value enables to discriminate between a high-energy portion of transmitted X-rays and a low-energy portion of transmitted X-rays, the high-energy portion comprising X-ray photons having an energy or wavelength below the threshold value and the low-energy portion comprising X-ray photons with energy or wavelength above such threshold value.

In prior art approaches, energy threshold values of detector elements of an X-ray detector are typically set on a global level prior to the actual X-ray examination, for example through a calibration procedure that optimizes for an average homogeneous object. Accordingly, there are no spatial variations in the threshold level values upon acquiring X-ray intensity values for each of the multiplicity of pixels of an acquired X-ray image.

However, it has been found that an object under examination affects not only the intensity of radiation transmitted through the object and then impinging onto the detector but also an energy distribution of an X-ray spectrum transmitted through the object is typically affected.

For instance, a highly attenuating dense object may shift the transmitted X-ray spectrum to higher energies compared to a weakly absorbing object because low-energy X-ray photons are typically more likely to get absorbed than high-energy X-ray photons. Such effect is also referred to as "beam hardening".

An idea underlying embodiments of the present invention is to, in generating an energy-resolved X-ray image, take into account such beam hardening effects. Particularly, in order to compensate for such effects, threshold value optimization should not be done on a global basis, i.e. energy threshold values should not be set identically in acquiring X-ray intensity values for all of the pixels of an energy-resolved X-ray image, but, instead, locally varying features of the object under examination should be taken into consideration.

In other words, it should be enabled that features of the object under examination may influence the energy threshold values applied when measuring an energy-depended intensity of X-rays transmitted through a region of interest for each of the multiplicity of pixels of an energy-resolved X-ray image.

According to embodiments of the present invention, it is therefore proposed to split the entire image acquisition process into two parts.

First, an X-ray beam is directed through the region of interest of the object and X-ray intensity values are acquired after transmission of the object. Therein, such X-ray intensity values are acquired for each of the pixels of the entire X-ray image to be generated. Such X-ray intensity values acquired in a first step will be referred to as "initial" X-ray intensity values and may be acquired using for example a relatively low X-ray dose. These initial X-ray intensity values may be used in a later processing step for generating the final energy-resolved X-ray image, although the main purpose of these values is to serve as an information basis for subsequently adapting an energy threshold value which may be set for subsequent acquisition of the "main" X-ray intensity values. In other words, the initial X-ray intensity values acquired in such preliminary acquisition may be used to determine local object features and characteristics and then set the threshold values spatially in relation to these local object features so that an optimal fraction of radiation may be detected for each part of the object. The initial X-ray intensity values may or may not be energy resolved, and/or may or may not be acquired with the same detector technology as the main X-ray intensity values.

Second, after setting the energy threshold values to values which have been adapted in dependence of the previously acquired initial X-ray intensity value for the respective pixel, the main X-ray intensity values from which all or the major part of the final energy-resolved X-ray image is to be generated may be acquired applying such set energy threshold values for each of the pixels.

Accordingly, at each pixel, i.e. for each location within the region of interest of the object, the local energy threshold values are specifically set depending on previously acquired initial X-ray intensity values for this location, i.e. taking into account the local X-ray attenuating properties of the object.

Accordingly, in generating an energy-resolved X-ray image, energy threshold values may be adapted in an optimum manner with respect to local X-ray attenuating characteristics of the examined object wherein the information about the local attenuating characteristics may be achieved by preceding acquiring initial X-ray intensity values at the respective location.

According to an embodiment of the invention, the acquiring of initial X-ray intensity values comprises acquiring first initial X-ray intensity values of X-rays transmitted through the region of interest within a first initial partial X-ray spectrum range at energies below a preset energy threshold value and acquiring second initial X-ray intensity values of X-rays transmitted through the region of interest within a second initial partial X-ray spectrum range at energies above the preset energy threshold value for each of the pixels respectively. The energy threshold value may then be adapted in dependence of the acquired first and second initial X-ray intensity values for each of the pixels.

In other words, the acquisition of the initial X-ray intensity values is already performed in an energy-resolved manner. Therein, an energy threshold value may be preset to a predefined value. Such predefined values may be for example identical for all pixels or may be estimated for each location of an examined object. Based on such preliminarily acquired initial X-ray intensity values, the energy threshold values may then be locally adapted for each of the pixels and subsequently a main energy-resolved image acquisition may be performed with such optimized energy threshold values.

For example, according to an embodiment of the invention, the energy threshold values may be adapted for each of the pixels such that the first main intensity values are substantially equal to the second main intensity values for each of the pixels.

In other words, the energy threshold values for each of the pixels may be adapted such that, in subsequent main image acquisition, the X-ray intensity values acquired for impinging X-rays having an energy lower than the threshold value and the intensity values acquired for impinging X-rays having an energy higher than the energy threshold value are substantially equal. Herein, "substantially equal" may be interpreted to enclose deviations from parity of up to 20% relative or alternatively of up to 10% relative.

According to an embodiment of the invention, an X-ray beam is scanned along a scanning path through the region of interest thereby simultaneously irradiating a sub-region of the region of interest, such sub-region corresponding to e.g. a sub-array of image pixel of the entire image. The initial X-ray intensity value for each of the pixels is acquired when the respective pixel is irradiated by an upstream portion of the scanning X-ray beam and the main first and main second X-ray intensity values for each pixel are acquired when the respective pixel is irradiated by a downstream portion of the scanning X-ray beam.

In other words, an X-ray beam and detector may be scanned through the region of interest. The X-ray beam and detector have cross section areas being as large as a multiplicity of adjacent pixels of the image to be acquired. Upon scanning the X-ray beam and detector, each part of the region of interest is therefore first illuminated by an upstream portion of the scanning X-ray beam, which is simultaneously detected by an upstream portion of the detector, and then subsequently illuminated by a downstream portion of this X-ray beam, which is detected by a downstream portion of the detector ("upstream" and "downstream" interpreted with respect to the scanning direction). Accordingly, the upstream portions of the X-ray beam and detector may be used for acquiring the initial X-ray intensity values. Based on these initial X-ray intensity values, the energy threshold value for a respective pixel or sub-region of the region of interest may then be suitably adapted. Accordingly, when the downstream portions of the X-ray beam and detector reach the respective pixels or sub-regions, main X-ray intensity values may be acquired using the previously adapted energy threshold value.

Thus, both the initial X-ray intensity values as well as the main X-ray intensity values for the energy-resolved X-ray image may be acquired in a single scanning process.

Therein, according to an embodiment, the initial X-ray intensity values and the main X-ray intensity values are acquired using an X-ray detector having a multiplicity of detector elements arranged along lines.

For example, such line detectors may be scanned with its longitudinal axes perpendicular to the scanning direction and one or more first detector lines may be used for acquiring an initial X-ray intensity value at a specific pixel or location in the region of interest before then, after further scanning the line detector, further downstream lines are used to acquire the first and second main X-ray intensity values having the associated energy threshold value already set to an optimized level based on the information provided by the first detector lines.

According to an alternative embodiment of the invention, an X-ray beam is directed through the region of interest simultaneously irradiating all pixels and the initial X-ray intensity values for each of the pixels are acquired simultaneously. Therein, in a subsequent step, an X-ray beam is directed through the region of interest simultaneously irradiating all pixels and the first and second main X-ray intensity values for each of the pixels are acquired simultaneously.

In other words, in contrast to the preceding embodiment, no scanning is performed but instead initial X-ray intensity values are acquired for the multiplicity of pixels simultaneously, then the energy threshold values are adapted for all pixels wherein each energy threshold value for one specific pixel is adapted in dependence of the acquired initial X-ray intensity value for the same pixel. Finally, the main image acquisition is performed by acquiring first and second main X-ray intensity values for first and second partial X-ray spectrum ranges at energies below and above the adapted energy threshold values, respectively.

In such embodiment, the initial X-ray intensity values and the first and second main X-ray intensity values may be acquired using an X-ray detector having a multiplicity of detector elements arranged as a 2-dimensional matrix.

In other words, the X-ray intensity values may be acquired using an X-ray detector having detector elements not only arranged along a line but arranged along a surface area such that, using such detector, a multiplicity of pixels of a 2-dimensional X-ray image may be acquired simultaneously.

According to an embodiment of the invention, the energy-resolved X-ray image is finally generated not only based on the first and second main X-ray intensity values for each pixel but on a or combination of the initial X-ray intensity values and the first and second main X-ray intensity values for each of the pixels.

In other words, the initial X-ray intensity values are not only acquired for subsequently adapting the energy threshold value for each of the pixels, but acquiring these initial X-ray intensity values is part of an entire X-ray intensity value acquisition such that the final energy-resolved X-ray image is generated based on these initial X-ray intensity values as well as based on subsequently acquired main X-ray intensity values. Accordingly, the information comprised in the preliminary initial X-ray intensity value acquisition may be reused for the final image. Thereby, exposure to excessive X-ray doses may be prevented.

It shall be noted that possible features and advantages of embodiments of the present invention are described herein partially with respect to an inventive method for generating an energy-resolved X-ray image and partially with respect to a device for generating such X-ray image. One skilled in the art will realize that features described with respect to the method may be applied in an analogue manner to the device and vice versa and that features may be combined or replaced in suitable manners such as to arrive at further embodiments of the invention.

BRIEF DESCRIPTION OF THE DRAWINGS

Subsequently, embodiments of the present invention will be described with respect to the attached drawings wherein neither the description nor the drawings shall be interpreted as limiting the invention.

The figures are only schematic and not to scale. Same reference signs relate to same or similar features throughout the figures.

DETAILED DESCRIPTION OF EMBODIMENTS

In the following description, possible features of the invention will be explained with respect to specific embodiments of the invention.

Generally, embodiments of the present invention relate to any energy-resolved X-ray imaging. Specific examples will be given below for mammography and computed tomography (CT) applications.

In energy-resolving X-ray imaging, an imaging system can discriminate between photon energies of detected X-rays and can hence assess spectral X-ray information. Several applications of energy-resolving detection, sometimes also referred to as spectral imaging, have been identified for example in the field of mammography, including energy weighting, energy subtraction and tissue characterization.

One example of an energy-resolving X-ray imaging system may be a photon-counting system. Such photon-counting system is for example provided by the applicant under the name "Philips MicroDose". In photon-counting detectors, a photon energy is typically measured by one or more discriminative energy thresholds. Therein, an intensity of X-rays reaching the detector may be measured both for X-rays having a photon energy below the threshold and for X-rays having a photon energy above the threshold.

A quality of the spectral information comprised in the final energy-resolved X-ray image typically depends on a setting of the threshold levels in relation to an energy spectrum of X-ray photons incident onto the detector. Accordingly, threshold optimization is required. As a trivial example, no spectral information is provided if all thresholds are out of a range of an incident X-ray spectrum and it is intuitively more efficient to put the threshold close to a centre of the X-ray spectrum incident onto the detector.

When an object is to be examined using X-ray imaging, a beam of X-rays is directed through a region of interest (ROI) of the object and X-ray intensity of X-rays transmitted through this ROI is measured. Internal structures within the object may have differing physical properties such as differing densities or material compositions and may thus have differing X-ray attenuating characteristics such that by measuring intensities of the transmitted X-rays, information about such internal structures may be derived.

However, the object under examination affects not only the intensity of transmitted X-radiation, but generally also affects an energy distribution of the transmitted X-ray spectrum. For instance, a highly attenuating dense portion of the object typically shifts the X-ray spectrum to higher energies compared to a weekly absorbing portion of the object because low-energy photons are more likely to get absorbed. This effect is commonly known as beam hardening.

Accordingly, while in prior art approaches, any energy thresholds of detector elements of an energy-resolving X-ray imaging device were generally set on a global level prior to an X-ray examination, for instance through a calibration procedure that optimizes for an average homogeneous object such that there are no spatial variations in the threshold level throughout an X-ray detection area of an X-ray detector, it is now proposed to take into account X-ray beam hardening and to at least partially compensate for such effect by implementing threshold optimization taking into consideration local object features and properties. Therein, embodiments of the present invention enable features and properties of the object under examination to influence the threshold levels of detector elements. Thus, a performance of spectral applications can be improved by optimizing the threshold values with respect to the object.

For example in mammography applications, locally varying object features and properties may be the breast thickness and breast glandularity (commonly referred to as breast density). Thicker and denser breasts generally shift a transmitted X-ray spectrum to higher energies.

In an alternative example of CT, locally varying object features and properties may be a thickness of a body part to be examined and tissue compositions. For instance, bones, blood, skin and thick body parts shift the transmitted X-ray spectrum to higher energies than fat, lung tissue and thin body parts.

Generally, in energy-resolved X-ray imaging according to embodiments of the present invention, an acquisition of X-ray intensity values of X-rays transmitted through a region of interest of an object is performed in two steps for each of the pixels of the energy-resolved X-ray image to be generated.

First, in an initial step, a preliminary X-ray intensity acquisition is performed. This preliminary X-ray acquisition may be typically taken with a low X-ray dose. Initial X-ray intensity values acquired in such preliminary step may then be used to determine the locally varying object features and properties, and threshold levels or values may be set in relation to these determined object features and properties so that, in a subsequent main acquisition step, an optimal fraction of X-radiation may be detected for each part or location of the examined object.

Then, in a main acquisition step, an X-ray beam of preferably higher dose than in the preliminary acquisition step may be directed through the ROI and X-ray intensity values may be acquired in an energy-resolved manner wherein the previously set optimized energy threshold values allow for optimized discriminating between X-ray photon energies in a lower spectrum portion below the energy threshold and photon energies in a higher spectrum portion above such threshold.

In principle, energy-resolved image acquisition may also be performed with more than one threshold, i.e. X-ray photons of more than two different spectrum portions may be distinguished and may be sorted into different "bins".

A first simple embodiment of the present invention directed to mammography applications will now be described with reference to FIGS. 1, 2 and 3.

Figure 1:
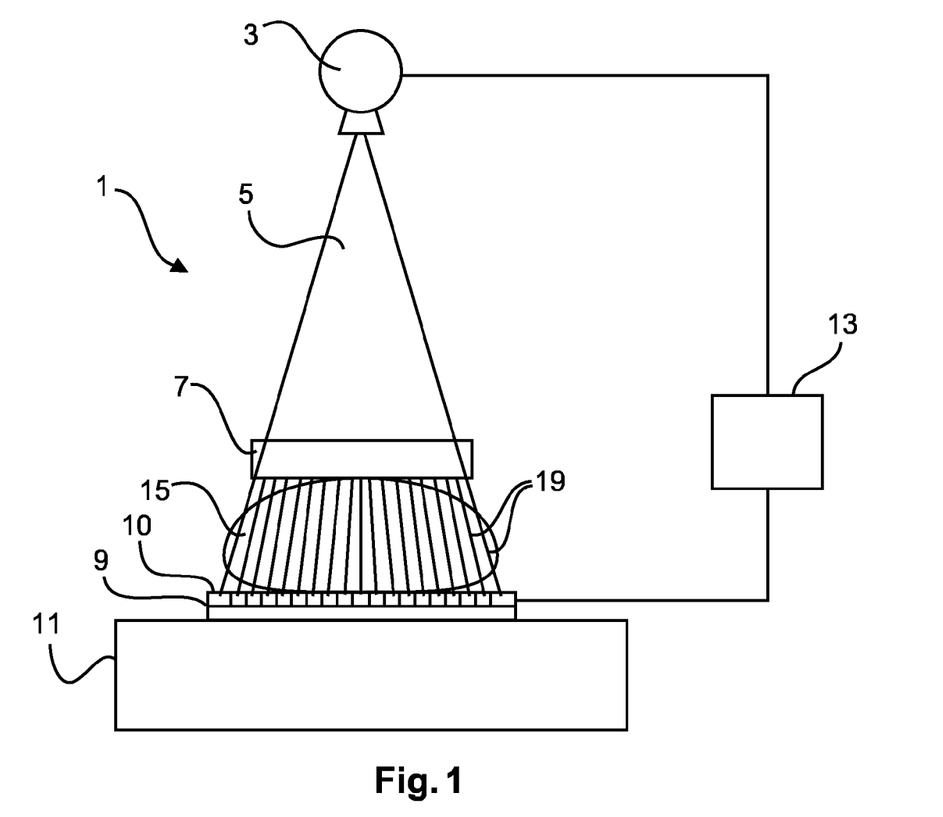
FIG. 1 shows a side view of a device for generating an energy-resolved X-ray image according to an embodiment of the present invention.

FIG. 1 shows a side view of a device 1 for generating an energy-resolved X-ray image comprising a multiplicity of pixels. The device 1 comprises an X-ray source 3 for generating an X-ray beam 5, a collimator 7, an X-ray detector 9, a support 11 and a control and evaluation unit 13.

The X-ray source 3 comprises an X-ray tube. The X-ray beam 5 is emitted by the X-ray source 3 with an emission angle such that an entire detection surface 10 of the X-ray detector 9 may be illuminated simultaneously. An object of interest 15 such as a female breast is arranged on top of the detection surface 10 of the X-ray detector 9 supported by the support 11 such that a region of interest is positioned on top of the detection surface 10.

Figure 2:
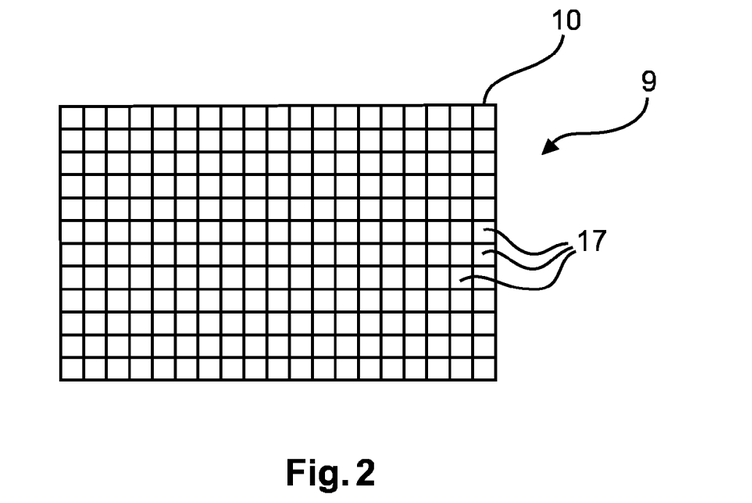
FIG. 2 shows a top view onto a 2D X-ray detector.

As shown in the top view of FIG. 2, the detection surface 10 of the X-ray detector 9 comprises a multiplicity of detector elements 17 arranged as a 2-dimensional matrix such that the detector elements 17 are arranged in a multiplicity of lines and rows. The collimator 7 collimates the X-ray beam 5 such that beam portions 19 are simultaneously directed to all of the detector elements 17 of the X-ray detector 9.

In such stationary arrangement, each of the detector elements 17 may generate a signal indicating an intensity of X-rays incident on this specific detector element 17. A multiplicity of such signals may then be provided to the control and evaluation unit 13. This control and evaluation unit 13 may evaluate the signals and finally generate an X-ray image comprising a multiplicity of pixels therefrom. Furthermore, the control and evaluation unit 13 may control an operation of the X-ray source 3 and of the detector 9.

In order to enable generating an energy-resolved X-ray image, the X-ray detector 9 is further adapted for discriminating between energy spectra of incident portions 19 of the X-ray beam 5. Particularly, each of the detector elements 17 may distinguish between incident X-ray photons having an energy lower than a threshold value and X-ray photons having an energy higher than a threshold value. Therein, the threshold value is not a fixed value but may be adapted and set for example by the control and evaluation unit 13. Particularly, the energy threshold value may be set for each of the multiplicity of detector elements 17 individually.

Accordingly, with a device 1 as shown in FIG. 1, a simple embodiment of a method for generating an energy-resolved X-ray image may be implemented and will be described with reference to the flow chart of FIG. 3.

After starting an X-ray image acquisition procedure (step S1), all components of the device 1 are initialized and operation parameters are set to predefined values (step S2). For example, parameters of the X-ray source 3 are preset such as to emit an X-ray beam 5 with a predefined energy spectrum. Furthermore, threshold values of the X-ray detector 9 are set to predefined values. Particularly, all energy threshold values for all detector elements 17 are generally set to an identical preset energy threshold value. Such preset energy threshold value may be determined for example based on a preceding calibration process.

Then, the X-ray source 3 is operated to emit and direct an X-ray beam 5 through a region of interest of the object 15. The X-ray detector 9 is controlled to acquire initial X-ray intensity values of X-rays transmitted through this ROI (step S3). In other words, a low-dose scout image is acquired prior to the actual main examination procedure.

The initial X-ray intensity values, i.e. the low-dose scout image, may or may not be acquired in an energy-resolving manner. However, it may be advantageous to acquire such initial intensity values in an energy-resolving manner, i.e. discriminating first initial X-ray intensity values of X-rays transmitted through the ROI within a first initial partial X-ray spectrum range at energies below a preset energy threshold value and second initial X-ray intensity values of X-rays transmitted through the ROI within a second initial partial X-ray spectrum range at energies above this preset energy threshold value for each of the detector elements 17.

Subsequently, the energy threshold value for each of the pixels, i.e. for each of the detector elements 17, is specifically adapted taking into account the previously acquired X-ray intensity values (step S4). In other words, the intensity values of the scout image are used to optimize the threshold values spatially. As the threshold values are adapted in dependence of the previously acquired X-ray intensity values for each of the pixels, local features and properties of the object 15 are taken into account upon such threshold value setting.

In a main examination and image acquiring step (steps S5 and S6) the X-ray beam 5 is again directed through the ROI of the object 15 (step S5) and main X-ray intensities are measured at each of the detector elements 17 of the X-ray detector 9 (step S6). Therein, the X-ray beam 5 is emitted with an X-ray spectrum and in acquiring the main X-ray intensity values, the detector elements 17 discriminate between X-ray photons within a first partial X-ray spectrum range at energies below the previously adapted energy threshold value for forming first main X-ray intensity values and X-ray photons having an energy within a second partial X-ray spectrum range at energies above the previously adapted energy threshold values for generating the second main X-ray intensity values.

Finally, from all the first and second main X-ray intensity values measured by the detector elements 17 of the X-ray detector 9, an energy-resolved X-ray image may be generated (step S7).

Therein, for example each of the main X-ray intensity values may form one pixel of the finally energy-resolved X-ray image and, therein, the first main X-ray intensity value may provide information about a low energy content and the second main X-ray intensity value may provide information about a high energy content of X-rays detected by the respective detector elements 17. Alternatively, a multiplicity of detector elements 17 may form a single pixel of the final energy-resolved X-ray image.

Figure 3:
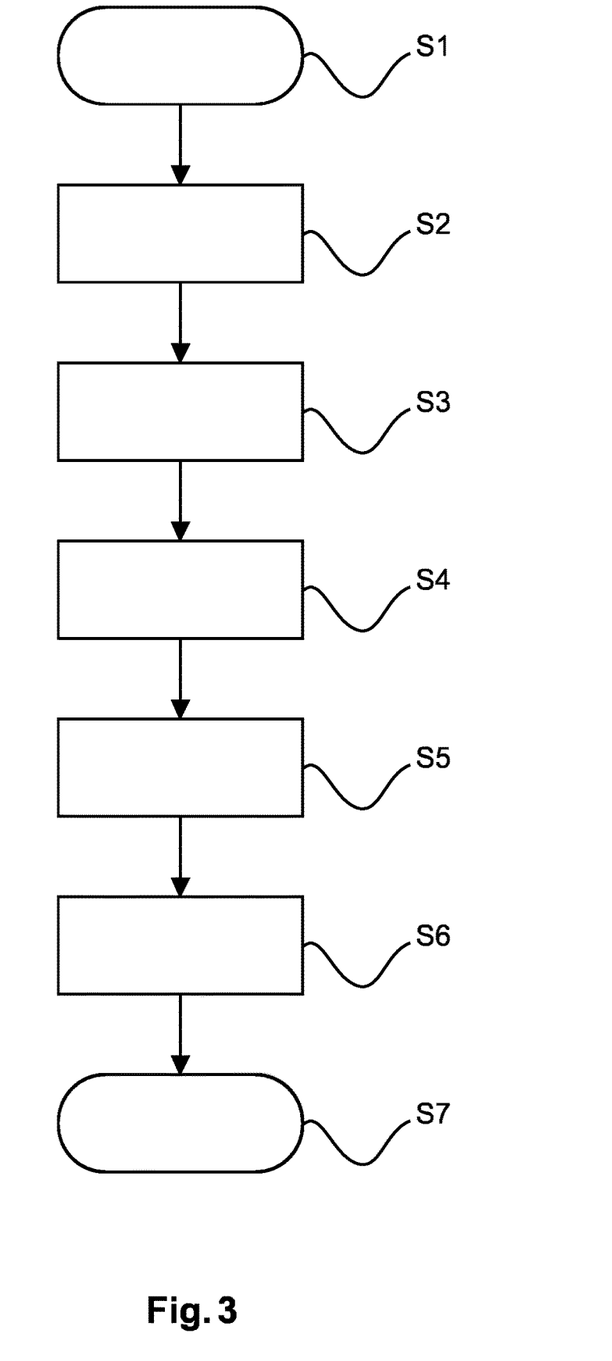
FIG. 3 shows a flow chart of a method for generating an energy-resolved X-ray image according to an embodiment of the present invention.

In the embodiment described with respect to FIGS. 1 to 3, X-ray intensity values are acquired for the entire ROI simultaneously. Therein, first a scout image is acquired, preferably at low X-ray dose, and then a main image is acquired. However, there is an inevitable time gap between such two image acquisitions which might add to motion blur. Due to such motion blur, the initial X-ray intensity values acquired for the scout image may not be useful to contribute to a final X-ray image. This may be generally suboptimal from an X-ray dose perspective and one therefore wants to minimize the time gap between acquisition of the initial and main X-ray intensity values. Further, two-dimensional photon-counting detectors are challenging and expensive to manufacture.

An embodiment forming a preferred implementation of the present invention will be described with respect to FIGS. 4 to 7. Therein, energy-resolved X-ray imaging is performed with a scanning system including a detector arrangement 9 with several consecutive line X-ray detectors having a multiplicity of detector elements 17 arranged along lines 18. An example of such scanning system is the "Philips MicroDose" mammography system.

Figure 4:
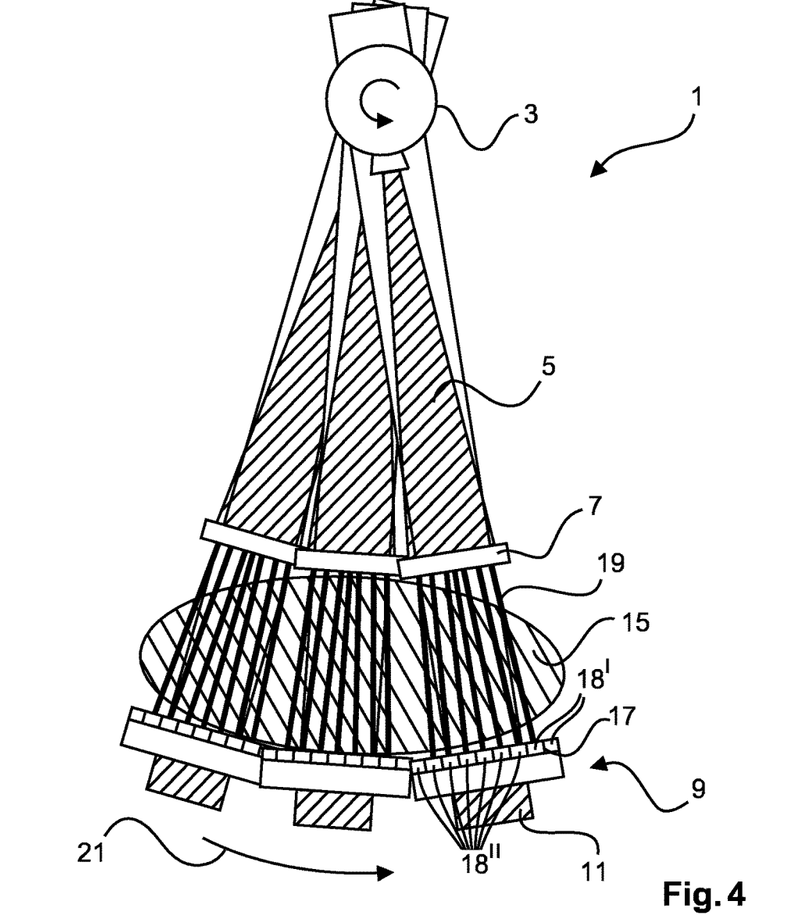
FIG. 4 shows a side view of a scanning device for generating an energy-resolved X-ray image according to another embodiment of the present invention.

Therein, an X-ray beam 5 emitted by a movable X-ray source 3 is scanned along a scanning path 21 through a region of interest of an object 15 such as a female breast.

Figure 5:
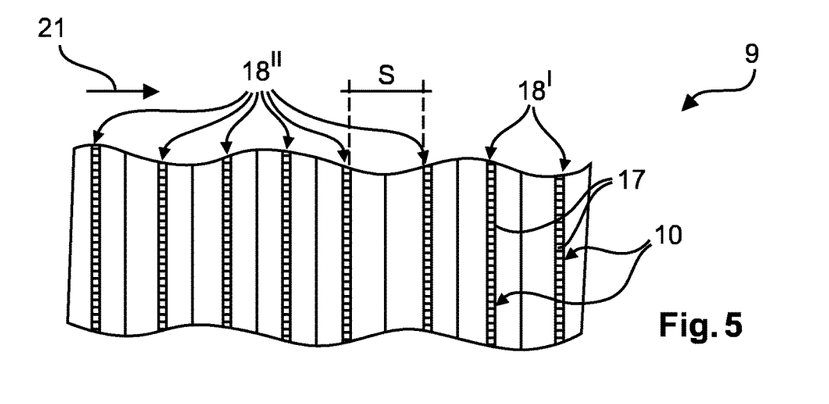
FIG. 5 shows a partial top view onto a line X-ray detector.
Figure 6:
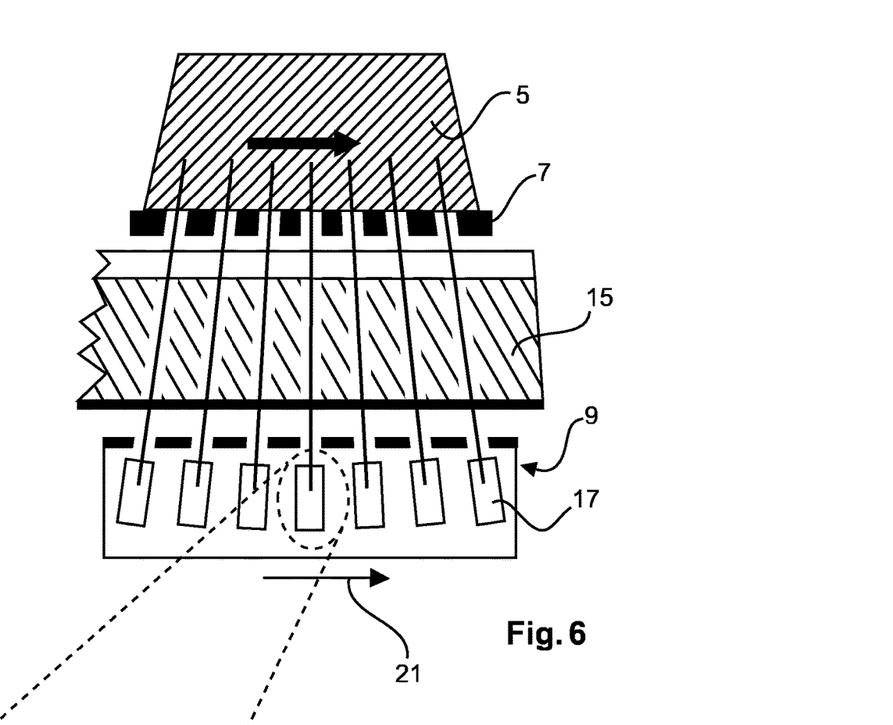
FIG. 6 shows an enlarged side view of a detector arrangement of a device as shown in FIG. 4.

As shown in the top view of FIG. 5, the X-ray detector arrangement 9 comprises several line X-ray detectors 18 each with a multiplicity of e.g. several thousands of detector elements 17 arranged one-dimensionally along lines. The lines detectors 18 are spaced from each other by a spacing s of e.g. a few millimeters while each of the detector elements 17 typically has dimensions in an order of 50 to 500 μm. As shown in FIGS. 4 and 5, the orientation of such line X-ray detectors is set perpendicular to the scanning direction 21.

While many of the method steps for generating an energy-resolved X-ray image using such scanning system are similar as described above with respect to the embodiment shown in FIGS. 1 to 3, there are also some significant and potentially beneficial differences.

Probably most important, in such scanning system, the energy threshold values of each of the detector elements 17 may be continuously optimized during a scanning procedure based for example on information obtained from a first line detector 18' or first line detectors 18' during the scan.

In other words, for an X-ray detector arrangement 9 with multiple detector lines 18 or elements 17, features of the object 15 at a specific position may be estimated from X-rays detected by for example first line detectors 18' of the detector 9 passing this position and may then be used to optimize the threshold values in the line detectors 18" passing the same position at a later point in time. Thereby, the time gap between acquisition of initial and main X-ray intensity values is minimized.

For example, at a start of a scanning procedure, the threshold values may be set using e.g. some conventional method and a best-guess of how the object may be composed. Then, during the scanning procedure, the X-ray beam 5 and the detector 9 are scanned along a scanning path 21 in a synchronized manner such that the X-ray beam 5 scans through the ROI of the object 15 and thereby simultaneously irradiates the detector elements 17 of the X-ray detector 9. These detector elements 17, for each position of the detector 9 during scanning, form a sub-array of several pixels of the image to be acquired.

During such scanning, initial X-ray intensity values may be acquired for each of the pixels when the respective pixel is irradiated by an upstream portion of the scanning X-ray beam 5 and detector 9. In other words, the initial X-ray intensity values may always be provided by one or several of the detector elements 17 of the first detector lines 18' along the scanning direction 21. Based on these initial X-ray intensity values, the energy threshold values of detector elements 17 of subsequent detector lines 18" in a downstream portion of the detector 9 may be specifically adapted before, subsequently, the main first and second X-ray intensity values are acquired by these detector elements 17.

In other words, at regular time points during a scan, energy thresholds of each detector element 17 are optimized based on energy-resolved or non-energy-resolved X-rays detected by previous detector lines during the scan. These time points may be adjusted to spaces between the detector lines and to a speed of the scanning motion.

Input to an optimization may be a feature/composition model of the object 15 under examination or any other optimization scheme. To predict features of the object 15 at positions not yet scanned by a part of the detector 9 in order to optimize the threshold values of the first detector lines, an assumption may be made that the object features are slowly varying in space and an extrapolation scheme may be applied.

The continuous optimization of energy threshold values may be implemented in electronics and/or software or firmware. For example, software in a computer program element may comprise computer-readable instructions which instruct a processor in a control and evaluation unit 13 to perform the described image acquisition method. The software may be stored in a computer-readable medium such as a CD, DVD, a flash memory or may be downloadable e.g. from a server via the internet.

The above described approach may be generalized to multi-row spiral CT, where a first detector row(s) may be used to tune the thresholds in accordance with the description above.

The X-ray detector in any of the implementations described above may be a photon-counting detector, such as in the Philips MicroDose system, or any other energy resolving detector in which threshold values can be set dynamically.

Figure 7:
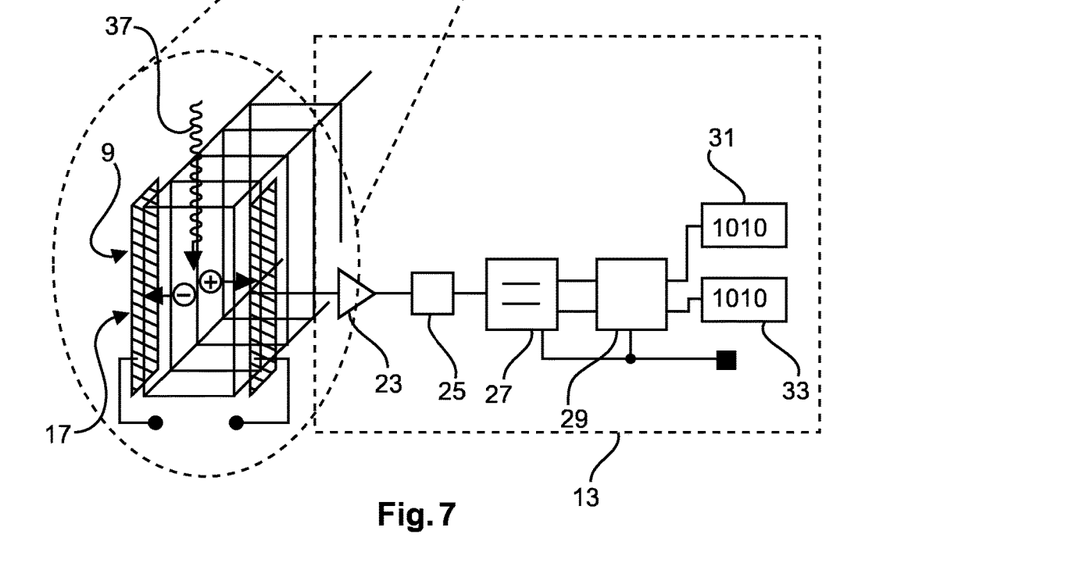
FIG. 7 shows a schematical representation of a detector element and an evaluation unit for an X-ray detector of a device for generating an energy-resolved X-ray image according to an embodiment of the present invention.

FIG. 7 shows basic principles of a detector element 17 of such detector 9 and of an evaluation and control unit 13 for data processing of signals provided by such detector 9. An X-ray photon 37 having a specific photon energy is captured within a detector element 17 and generates a charge couple between two electrodes set under high voltage. A voltage signal is provided to a preamplifier 23, a shaper 25, a discriminator 27, an anti-coincidence unit 29 and finally two counters 31, 33 included in the evaluation and control unit 13. Using such arrangement, an energy of the X-ray photon 37 may be resolved and, depending on this energy being higher or lower than a threshold value, occurrence of the X-ray photon 37 will be counted in one of the counters 31, 33.

It shall be noted that, in analogy with the above described single X-ray source 3 and multiple detector lines 17, inverse imaging geometries having one detector and multiple X-ray sources are also possible. Aspects of the invention can be generalized to such geometries by, instead of adjusting the energy threshold, adjusting the input spectrum, for instance the kVp for filtering of the individual X-ray sources.

Embodiments of the invention may be applied to any spectral application. Optimized threshold values may improve a performance of energy weighting, enabling better image quality in terms of higher contrast-to-noise-ratio or equal image quality at lower dose. Optimized thresholds may be also important for energy subtraction (also known as dual-energy subtraction) as well as for tissue characterization such as lesion characterization or breast density assessment.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A device for generating an energy-resolved X-ray image comprising a multiplicity of pixels, wherein the device comprises:
   an X-ray source;
   an X-ray detector;
   an adapting means; and
   a control and evaluation unit;
   wherein the X-ray source is configured to direct an X-ray beam through a region of interest of an object;

wherein the X-ray detector is configured to acquire initial X-ray intensity values of X-rays transmitted through the region of interest for each of the pixels;

wherein the adapting means are configured to adapt an energy threshold value for each pixel in dependence of the acquired X-ray intensity values for each of the pixels; and wherein the X-ray source is further configured to direct an X-ray beam having an X-ray spectrum through the region of interest of the object;

wherein the X-ray detector is further configured to acquire first main X-ray intensity values of X-rays transmitted through the region of interest within a first partial X-ray spectrum range at energies below the adapted energy threshold value and to acquire second main x-ray intensity values of X-rays transmitted through the region of interest within a second partial X-ray spectrum range at energies above the adapted energy threshold value for each of the pixels, respectively; and wherein the control and evaluation unit is configured to generate the energy-resolved X-ray image based on the first and second main x-ray intensity values for each of the pixels.

2. The device of claim 1, wherein the X-ray source is further configured to generate an X-ray beam; and wherein the X-ray detector is further configured to discriminate an energy of detected X-rays being below or above the energy threshold value.

3. The device of claim 2, wherein
the X-ray detector is further configured to acquire first initial X-ray intensity values of X-rays transmitted through the region of interest within a first initial partial X-ray spectrum range at energies below a preset energy threshold value and acquire second initial x-ray intensity values of X-rays transmitted through the region of interest within a second initial partial X-ray spectrum range at energies above the preset energy threshold value for each of the pixels, respectively; and the adapting means is further configured to adapt the energy threshold value in dependence of the acquired first and second initial X-ray intensity values for each of the pixels.

4. The device of claim 2, wherein the adapting means is further configured to adapt the energy threshold value for each of the pixels such that the first initial intensity values are substantially equal to the second initial intensity values for each of the pixels.

5. A method for generating an energy-resolved X-ray image comprising a multiplicity of pixels, comprising:
directing an X-ray beam through a region of interest of an object and acquiring initial X-ray intensity values of X-rays transmitted through the region of interest for each of the pixels;
adapting an energy threshold value for each pixel in dependence of the acquired X-ray intensity values for each of the pixels; and
directing an X-ray beam having an X-ray spectrum through the region of interest of the object and acquiring first main X-ray intensity values of X-rays transmitted through the region of interest within a first partial X-ray spectrum range at energies below the adapted energy threshold value and acquiring second main X-ray intensity values of X-rays transmitted through the region of interest within a second partial X-ray spectrum range at energies above the adapted energy threshold value for each of the pixels, respectively;
generating the energy-resolved X-ray image based on the first and second main x-ray intensity values for each of the pixels.

6. The method according to claim 5, wherein the acquiring of the initial X-ray intensity values comprises acquiring first initial X-ray intensity values of X-rays transmitted through the region of interest within a first initial partial X-ray spectrum range at energies below a preset energy threshold value and acquiring second initial x-ray intensity values of X-rays transmitted through the region of interest within a second initial partial X-ray spectrum range at energies above the preset energy threshold value for each of the pixels, respectively, and
wherein the energy threshold value is adapted in dependence of the acquired first and second initial X-ray intensity values for each of the pixels.

7. The method according to claim 6, wherein the energy threshold value is adapted for each of the pixels such that the first main intensity values are substantially equal to the second main intensity values for each of the pixels.

8. The method according to claim 5, wherein an X-ray beam is scanned along a scanning path through the region of interest thereby simultaneously irradiating a sub-array of several pixels in a portion of the region of interest and wherein the initial X-ray intensity value for each of the pixels is acquired when the respective pixel is irradiated by an upstream portion of the scanning X-ray beam and the main first and second X-ray intensity value for each of the pixels is acquired when the respective pixel is irradiated by a downstream portion of the scanning X-ray beam, wherein up- and downstream is interpreted with respect to the scanning direction.

9. The method according to claim 8, wherein the initial X-ray intensity values and the main X-ray intensity values are acquired using an X-ray detector having several line detectors each with a multiplicity of detector elements arranged along a line.

10. The method according to claim 5, wherein an X-ray beam is directed through the region of interest simultaneously irradiating all pixels of the entire region of interest, and the initial X-ray intensity values for each of the pixels are acquired simultaneously and wherein, in a subsequent step, an X-ray beam is directed through the region of interest simultaneously irradiating all pixels and the first and second main X-ray intensity values for each of the pixel are acquired simultaneously.

11. The method according to claim 10, wherein the initial X-ray intensity values and the first and second main X-ray intensity values are acquired using an X-ray detector having a multiplicity of detector elements arranged as a 2-dimensional matrix.

12. The method according to claim 5, wherein the energy-resolved X-ray image is generated based on a combination of the initial X-ray intensity values and the first and second main x-ray intensity values for each of the pixels.

13. An X-ray imaging system comprising an X-ray source, an X-ray detector, and a computer programmed to perform a method for generating an energy-resolved X-ray image comprising a multiplicity of pixels, comprising: directing an X-ray beam through a region of interest of an object and acquiring initial X-ray intensity values of X-rays transmitted through the region of interest for each of the pixels; adapting an energy threshold value for each pixel in dependence of the acquired X-ray intensity values for each of the pixels; and directing an X-ray beam having an X-ray spectrum through the region of interest of the object and acquiring first main X-ray intensity values of X-rays transmitted through the region of interest within a first partial X-ray spectrum range at energies below the adapted energy threshold value and acquiring second main X-ray intensity values of X-rays transmitted through the region of interest within a second partial X-ray spectrum range at energies above the adapted energy threshold value for each of the pixels, respectively; generating the energy-resolved X-ray image based on the first and second main x-ray intensity values for each of the pixels.

14. A non-transitory computer readable medium having a computer program stored thereon which computer program is configured to control a computer to carry out a method for generating an energy-resolved X-ray image comprising a multiplicity of pixels, comprising: directing an X-ray beam through a region of interest of an object and acquiring initial X-ray intensity values of X-rays transmitted through the region of interest for each of the pixels; adapting an energy threshold value for each pixel in dependence of the acquired X-ray intensity values for each of the pixels; and directing an X-ray beam having an X-ray spectrum through the region of interest of the object and acquiring first main X-ray intensity values of X-rays transmitted through the region of interest within a first partial X-ray spectrum range at energies below the adapted energy threshold value and acquiring second main X-ray intensity values of X-rays transmitted through the region of interest within a second partial X-ray spectrum range at energies above the adapted energy threshold value for each of the pixels, respectively; generating the energy-resolved X-ray image based on the first and second main x-ray intensity values for each of the pixels.

15. An X-ray imaging system comprising:
   an X-ray source;
   an X-ray detector including a plurality of detector pixels, the X-ray source and the X-ray detector being disposed across a region for receiving an object to be imaged;
   a display device; and
   one or more computer processors configured to:
      control the X-ray source to direct an X-ray beam having an X-ray spectrum through the region for receiving the object and control the X-ray detector to acquire first X-ray intensity values of X-rays transmitted through the region for receiving the object within a first partial X-ray spectrum range at energies below an energy threshold value and acquire second X-ray intensity values of X-rays transmitted through the region of interest within a second partial X-ray spectrum range at energies above the energy threshold value for each of the pixels, respectively,
      adjust the energy threshold based on the acquired first and second X-ray intensity values for each pixel,
      control the X-ray source to continue directing the X-ray beam through the region for receiving the object and control the X-ray detector to continue to acquire the first and second energy values with the adjusted energy threshold,
      generate an energy-resolved X-ray image based on the first and second X-ray intensity values for each of the pixels, and
      control the display device to display the energy-resolved X-ray image.

16. The system according to claim 15, wherein the energy threshold is adjusted such that the first intensity values are substantially equal to the second intensity values for each of the pixels.

17. The system according to claim 15, wherein the X-ray detector includes a plurality of subarrays of pixels and further including a drive connected with at least one of the X-ray source and the X-ray detector, and wherein the one or more computer processors are further configured to:
   scan the X-ray beam along a scanning path simultaneously irradiating each subarray and wherein an initial X-ray intensity value for each of the pixels is acquired when the respective pixel is irradiated by an upstream portion of the scanning X-ray beam and the first and second X-ray intensity values for each pixel are acquired when the respective pixel is irradiated by a downstream portion of the scanning X-ray beam, wherein upstream and downstream are interpreted with respect to the scanning direction.

18. The system according to claim 17, wherein the subarrays of pixels include a plurality of lines of detector elements arranged parallel to each other and transverse to the scanning path.

19. The system according to claim 15, wherein the one or more computer processors are further configured to readjust the energy thresholds and regular time points during a scan.

* * * * *